United States Patent
Haddad et al.

(10) Patent No.: US 9,176,104 B2
(45) Date of Patent: *Nov. 3, 2015

(54) PREDICTING ODOR PLEASANTNESS WITH AN ELECTRONIC NOSE

(71) Applicant: Yeda Research and Development Co. Ltd., Rehovot (IL)

(72) Inventors: Rafi Haddad, Rehovot (IL); Noam Sobel, Jaffa (IL); David Harel, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/530,903

(22) Filed: Nov. 3, 2014

(65) Prior Publication Data

US 2015/0051842 A1    Feb. 19, 2015

Related U.S. Application Data

(63) Continuation of application No. 13/386,445, filed as application No. PCT/IL2010/000587 on Jul. 22, 2010, now Pat. No. 8,880,448.

(60) Provisional application No. 61/323,945, filed on Apr. 14, 2010, provisional application No. 61/227,821, filed on Jul. 23, 2009.

(51) Int. Cl.
| | |
|---|---|
| *G06N 5/00* | (2006.01) |
| *G06F 1/00* | (2006.01) |
| *G01N 33/00* | (2006.01) |
| *G06N 99/00* | (2010.01) |

(52) U.S. Cl.
CPC ........ *G01N 33/0073* (2013.01); *G01N 33/0034* (2013.01); *G06N 99/005* (2013.01)

(58) Field of Classification Search
USPC .......................................................... 706/20
See application file for complete search history.

(56) References Cited

U.S. PATENT DOCUMENTS

| | | | |
|---|---|---|---|
| 7,413,731 B2 * | 8/2008 | Heltovics et al. ............ | 424/76.4 |
| 2003/0022082 A1 | 1/2003 | Ohmura et al. | |
| 2006/0191319 A1 * | 8/2006 | Kurup ........................ | 73/23.34 |

(Continued)

FOREIGN PATENT DOCUMENTS

| | | |
|---|---|---|
| EP | 1336844 | 8/2003 |
| WO | WO 2013/035070 | 3/2013 |
| WO | WO 2015/037003 | 3/2015 |

OTHER PUBLICATIONS

International Preliminary Report on Patentability Dated Mar. 20, 2014 From the International Bureau of WIPO Re. Application No. PCT/IB2012/054621.

(Continued)

*Primary Examiner* — Jeffrey A Gaffin
*Assistant Examiner* — Kalpana Bharadwaj

(57) ABSTRACT

Apparatus and method for assessing odors, comprises an electronic nose, to be applied to an odor and to output a structure identifying the odor; a neural network which maps an extracted structure to a first location on a pre-learned axis of odor pleasantness; and an output for outputting an assessment of an applied odor based on said first location. The assessment may be a prediction of how pleasant a user will consider the odor.

20 Claims, 11 Drawing Sheets
(9 of 11 Drawing Sheet(s) Filed in Color)

(56) References Cited

U.S. PATENT DOCUMENTS

| | | | |
|---|---|---|---|
| 2007/0191257 A1 | 8/2007 | Andretta et al. | |
| 2008/0188172 A1* | 8/2008 | Hollemans et al. | 454/75 |
| 2010/0024533 A1* | 2/2010 | Kimura et al. | 73/73 |
| 2012/0143804 A1 | 6/2012 | Haddad et al. | |
| 2014/0221269 A1 | 8/2014 | Sobel et al. | |

OTHER PUBLICATIONS

International Search Report and the Written Opinion Dated Dec. 15, 2014 From the International Searching Authority Re. Application No. PCT/IL2014/050812.

International Search Report and the Written Opinion Dated Jan. 16, 2013 From the International Searching Authority Re. Application No. PCT/IB2012/054621.

International Search Report and the Written Opinion Dated Nov. 30, 2010 From the International Searching Authority Re. Application No. PCTIL2010/000587.

Official Action Dated Nov. 18, 2013 From the US Patent and Trademark Office Re. U.S. Appl. No. 13/386,445.

Aron "White Noise for Your Nose Cancels Pungent Aromas", New Scientist, Issue 2993, Oct. 30, 2014.

Baldi et al. "When Is Chemical Similarity Significant? The Statistical Distribution of Chemical Similarity and Its Extreme Values", Journal of Chemical Information and Modeling, 50(7): 1205-1222, Jul. 26, 2010.

Burl et al. "Assessing the Ability to Predict Human Percepts of Odor Quality From the Detector Responses of a Conducting Polymer Composite-Based Electronic Nose", Sensor & Actuators: B Chemical, 72(2): 149-159, 2001.

Dutta et al. "Tea Quality Prediction Using A Tin Oxide-Based Electronic Nose: An Artificial Intelligence Approach", Sensors and Actuators B, XP004443608, 94(2): 228-237, Sep. 1, 2003. P.230, § 1.4, Fig.1, P.235, § 4.1, P.237, 1-h Col., Lines 19-27.

Haddad et al. "A Metric for Odorant Comparison", Nature Methods, 5(5): 425-429, May 2008.

Haddad et al. "Global Features of Neural Activity in the Olfactory System Form A Parallel Code That Predicts Olfactory Behavior and Perception", The Journal of Neuroscience, 30(27): 9017-9026, Jul. 7, 2010.

Haddad et al. "Measuring Smells", Current Opinion in Neurobiology, 18(4): 438-444, Aug. 31, 2008.

Harel et al. "Towards An Odor Communication System", Computational Biology and Chemistry, 27(2): 121-133, May 2003.

Howard "'White Noise' for Your Nose Cancels Out Nasty Odor", The Huffington Post, Nov. 2, 2014.

Khan et al. "Predicting Odor Pleasantness From Odorant Structure: Pleasnatness as A Reflection of the Physical World", The Journal of Neuroscience, 27(37): 10015-10023, Sep. 12, 2007.

Mamlouk et al. "On the Dimensions of the Olfactory Perception Space", Neurocomputing, 58-60: 1019-1025, Jun. 30, 2004.

Pardo et al. "Electronic Nose for Coffee Quality Control", Proceedings of the 18th IEEE Instrumentation and Measurement Technology Conference, Budapest, Hungary, May 21-23, 2001, IMTC 2001, XP010546673, 1: 123-127, May 21, 2001.

Saito et al. "Odor Coding by A Mammalian Receptor Repertoire", Science Signaling, 2(60): 1-28, Mar. 3, 2009.

Twin et al. "Smell Peak Prediction During Black Tea Fermentation Process Using Time-Delay Neural Network on Electronic Nose Data", Proceedings of the International Conference on Computing: Theory and Applications, ICCTA'07, XP031058246, P.257-260, Mar. 1, 2007.

Varshney et al. "Olfactory Signals and Systems", arXiv Reprint, 4110.4864(1): 1-13, Oct. 17, 2014.

Communication Pursuant to Rule 164(1) EPC: Supplementary Partial European Search Report Dated May 11, 2015 From the European Patent Office Re. Application No. 12830464.9.

Restriction Official Action Dated Sep. 1, 2015 From the US Patent and Trademark Office Re. U.S. Appl. No. 14/343,064.

* cited by examiner

PREDICTING ODOR PLEASANTNESS WITH AN ELECTRONIC NOSE

RELATED APPLICATIONS

This application is a continuation of U.S. patent application Ser. No. 13/386,445 filed on Feb. 27, 2012, which is a National Phase of PCT Patent Application No. PCT/IL2010/000587 having International filing date of Jul. 22, 2010, which claims the benefit of priority under 35 USC §119(e) of U.S. Provisional Patent Application Nos. 61/323,945 filed on Apr. 14, 2010 and 61/227,821 filed on Jul. 23, 2009. The contents of the above applications are all incorporated by reference as if fully set forth herein in their entirety.

FIELD AND BACKGROUND OF THE INVENTION

The present invention relates to a device and method for predicting odor pleasantness using an electronic nose.

In 1968, Dravnieks envisioned an artificial or electronic nose as an instrument that would inspect samples of odorous air and report the intensity and quality of an odor without the intervention of a human nose. Although eNoses have since been developed, they serve primarily in tasks of odor detection and discrimination but not for reporting odor quality.

The main component of an eNose is an array of non-specific chemical sensors. An odor analyte stimulates many of the sensors in the array and elicits a characteristic response pattern. The sensors inside eNoses can be made of a variety of technologies, but in all cases a certain physical property is measured and a set of signals is generated. The stages of the recognition process are similar to those of biological olfaction, where a sensor responds to more than one odorant and one odorant activates more than one sensor. Together, the set of activated sensors and their signals characterize the odor, sometimes referred as an odor fingerprint. Thus, an important difference between eNoses and analyte detectors such as gas chromatographs, is that whereas the latter are aimed at identifying the components that contribute to an odor, eNoses can be used to identify, as a whole, the mixture of components that together form an odor. Despite the promise of an artificial system that may substitute for olfaction, very few efforts have been made to use eNoses in tasks that go beyond detection and discrimination. A notable exception are the efforts to develop eNoses for medical diagnosis. In such efforts eNoses were used to identify the disease as a whole, rather than particular analytes that relate to it. In a previous proposal the present inventors linked eNose measurements to olfactory activity in olfactory receptor neurons suggesting that an eNose can capture the odor attributes relevant to biological receptors. Here we set out to ask whether eNose measurements can similarly be linked to olfactory perception. This effort may be more complicated than linking eNose output to receptor response. because perception is governed not only by stimulus structure, but also by higher-order mechanisms such as experience and learning.

To date, the only effort to report perceptual qualities using an eNose was by Burl et al (Burl et al. 2001). Using an array of conducting polymer composite detectors they predicted 17 odor qualities for each of 20 odorants by using a "leave one out" scheme, and a battery of prediction algorithms. Although significant prediction rates were obtained for a portion of the odor qualities, the result did not generalize to novel odorants. Burl et al (Burl et al. 2001) postulated that this outcome may have reflected the small number of odorants they used. Burl et al (Burl et al. 2001) focused their efforts on predicting discreet perceptual characteristics, for example minty and floral.

SUMMARY OF THE INVENTION

An ideal artificial nose should be able to smell and report the perceptual qualities of novel odors. Currently, however, artificial noses, known as electronic noses (eNose), primarily detect and discriminate between odors they have previously "learned".

In contrast to Burl above, the present embodiments focus on perceptual axes, so that useful conclusions may be reached about new odours. Several lines of evidence suggest that the primary perceptual axis of human olfaction is odorant pleasantness. Furthermore, psychophysical evidence suggested that odorant pleasantness is reflected in part in the physicochemical structure of odorant molecules. With this link in mind, the present embodiments show that an eNose can be tuned to some kind of a pleasantness scale, and then used to predict the pleasantness of novel odours.

According to one aspect of the present invention there is provided a method of assessing odors, comprising:
 providing an electronic nose;
 applying said electronic nose to an odor;
 extracting odor information of said odor using said electronic nose;
 plotting said extracted odor information to a first location on an axis of odor pleasantness via a pre-learnt neural network; and
 outputting an assessment based on said first location.

In an embodiment, said axis of odor pleasantness comprises a linear succession of mappings of odor signatures to gradings of pleasantness.

An embodiment may comprise providing said pre-learned neural network for said axis of odor pleasantness by:
 providing assessors with a series of odor samples;
 obtaining pleasantness scores from each assessor;
 extracting odor information of said samples using said electronic nose; and
 training said neural network to correlate said scores with said extracted odor information by mapping said odor information to a linear succession of said scores.

In an embodiment, said odor information is obtained within said electronic nose by extracting features from signals output by sensors of said nose.

An embodiment may comprise minimizing said features to a minimal set that allows convergence of same odors and divergence of different odors.

An embodiment may comprise assessing the pleasantness of an odor having odor information not used in setting up said pre-trained neural network, by mapping to said axis using said neural network.

An embodiment may comprise hardwiring a region of said axis to an indication of unpleasantness.

An embodiment may comprise associating parts of said region with respective predetermined compact molecules.

An embodiment may comprise setting up said axis according to measures of molecular compactness.

According to a second aspect of the present invention there is provided an apparatus for assessing odors, comprising:
 an electronic nose, configured to be applied to an odor and to output a structure identifying said odor;
 a neural network, pretrained with odors and corresponding pleasantness gradings, for mapping an extracted structure to a first location on an axis of odor pleasantness; and an output for outputting an assessment of an applied odor based on said first location.

In an embodiment, said axis of odor pleasantness comprises a linear succession of mappings of odor signatures to gradings of pleasantness.

In an embodiment, said axis of odor pleasantness comprises a plurality of structures from test odors ordered according to assessments of pleasantness provided by assessors.

In an embodiment, said structure is obtained within said electronic nose using signal output features of sensors of said electronic nose.

In an embodiment, said structures represent odor information of chemical content of said odors according to a plurality of non-specific chemical sensors.

In an embodiment, said neural network is configured to plot a structure not present in said axis, by comparing with closest structures in said axis, thereby to identify a respective first location.

An embodiment may comprise a region of said axis being hardwired to an indication of unpleasantness.

An embodiment may involve parts of said region being associated with respective predetermined compact molecules.

In an embodiment, said axis is calibrated according to measures of molecular compactness.

Unless otherwise defined, all technical and scientific terms used herein have the same meaning as commonly understood by one of ordinary skill in the art to which this invention belongs. The materials, methods, and examples provided herein are illustrative only and not intended to be limiting.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Implementation of the method and/or system of embodiments of the invention can involve performing or completing selected tasks manually, automatically, or a combination thereof. This refers in particular to tasks involving the control of the electronic nose and associated odor processing.

Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawings will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a simplified flow diagram illustrating a method of assessing or predicting smell pleasantness according to the present embodiments;

FIG. 2 is a block diagram which shows an apparatus for providing the method of FIG. 1;

FIG. 3 shows results for training a neural network on a set of odors and pleasantness assessments, according to an embodiment of the present invention;

FIGS. 4A and 4B show results for predicting pleasantness of unseen odors according to an embodiment of the present invention;

FIG. 5 is a simplified diagram showing how different numbers of samples improve prediction power according to another embodiment of the present invention;

Figure 6A:
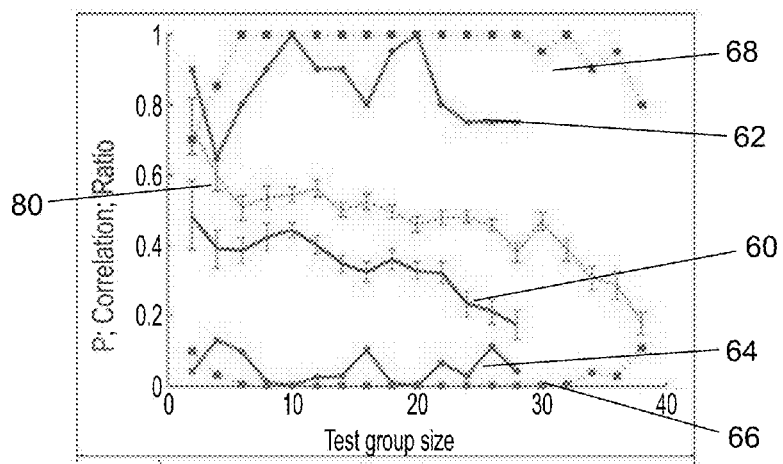
Figure 6B:
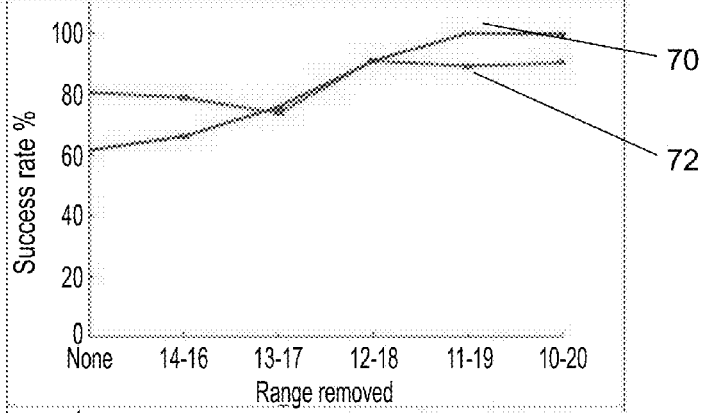
Figure 6C:
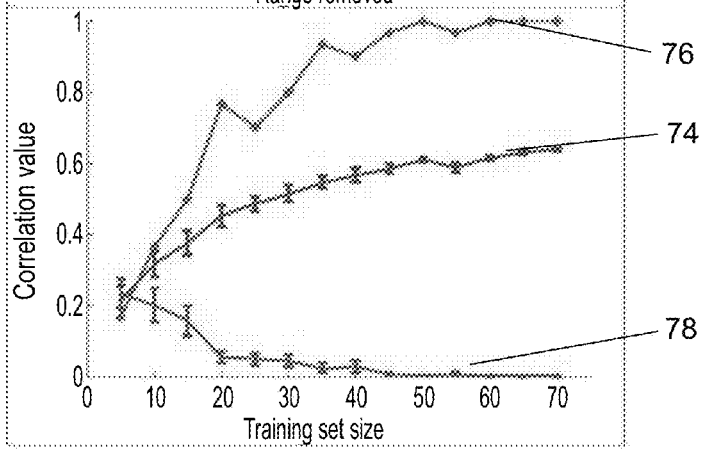
Figure 7A:
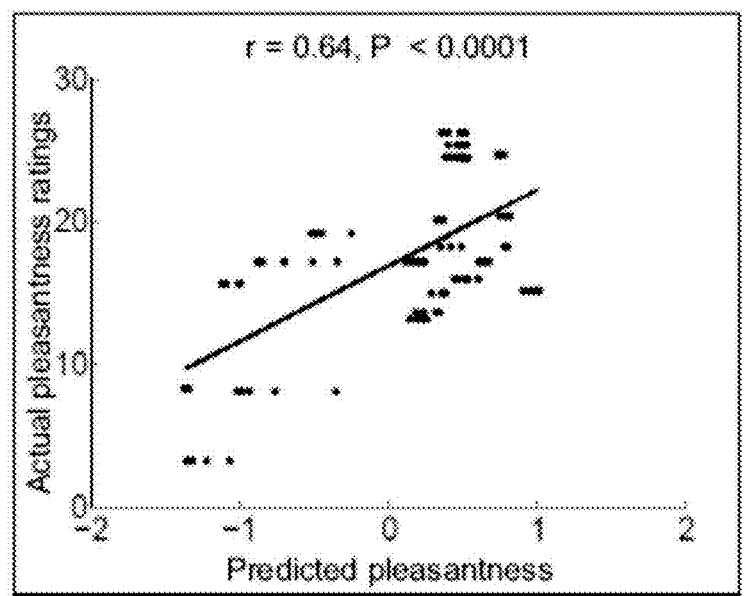
Figure 7B:
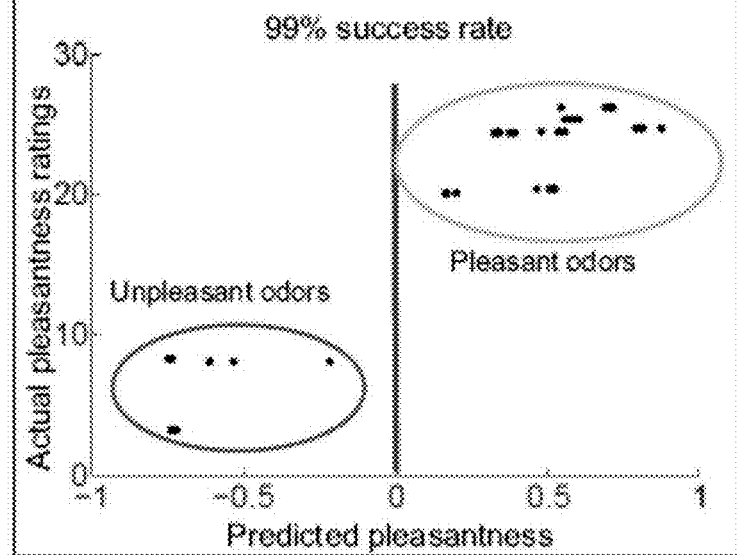
Figure 8A:
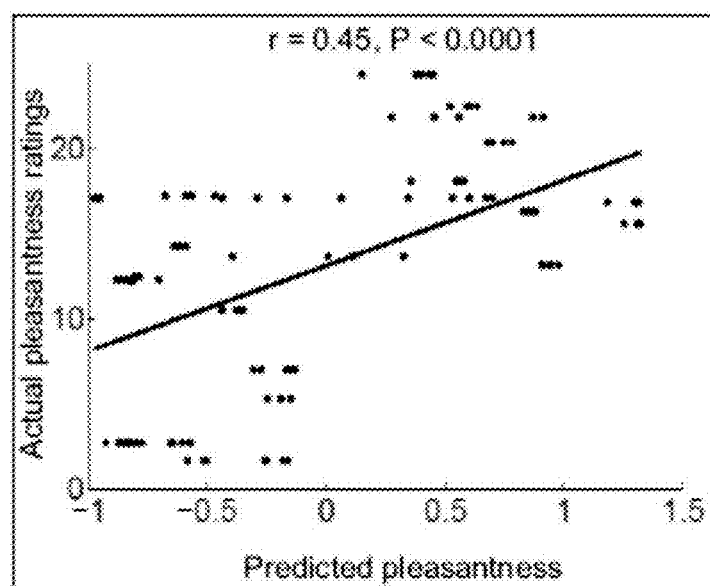
Figure 8B:
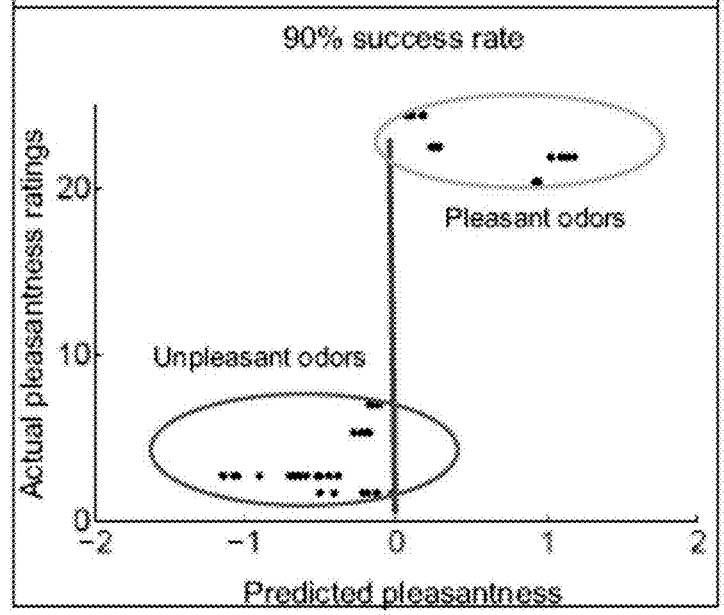
Figures 9A, 9B, 9C, 9D:
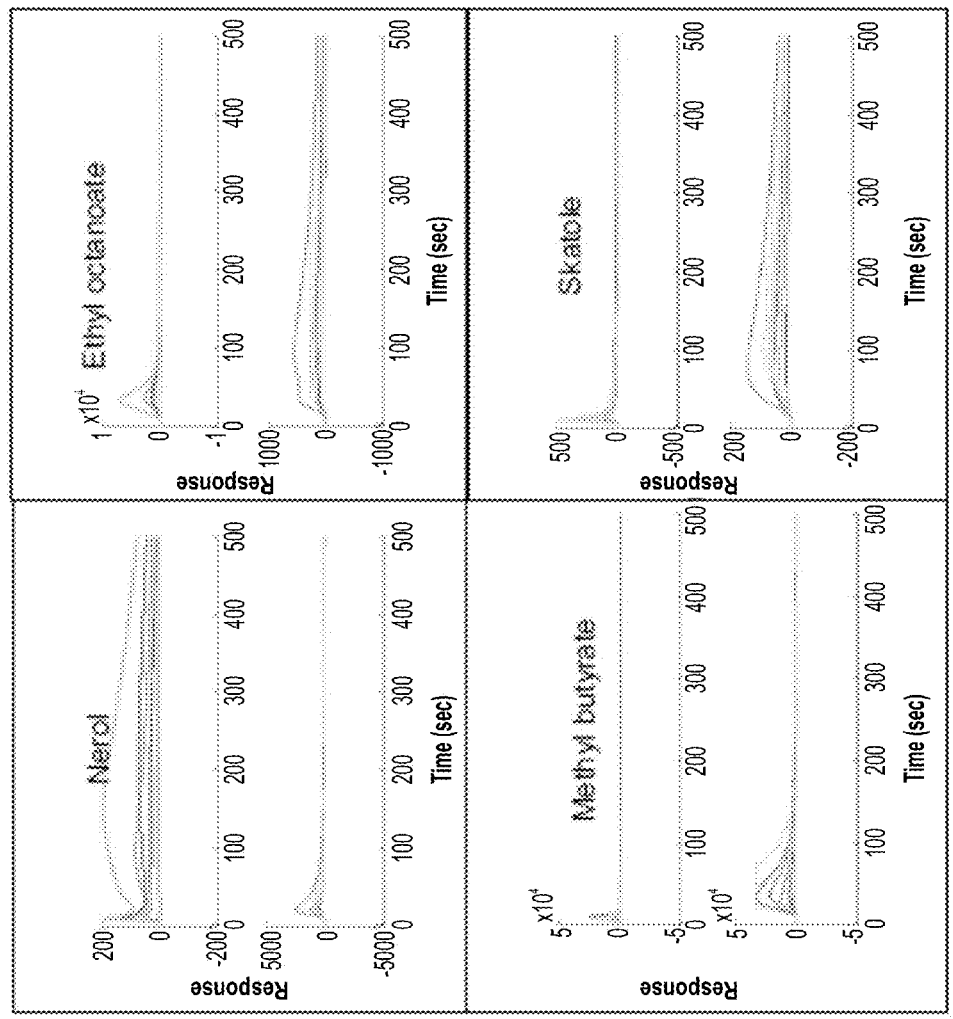
Figure 10A:
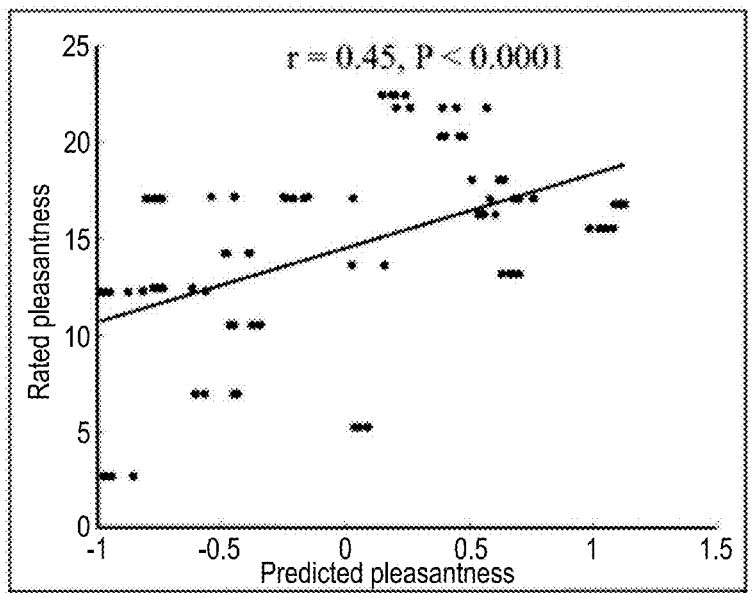
Figure 10B:
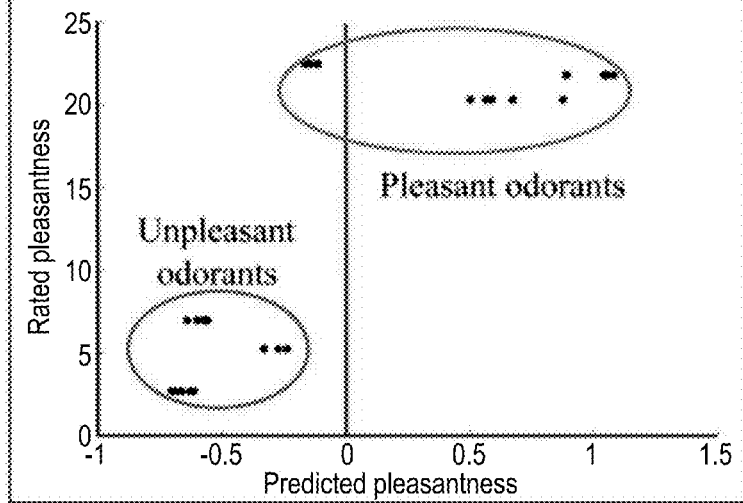
Figures 11A, 11B:
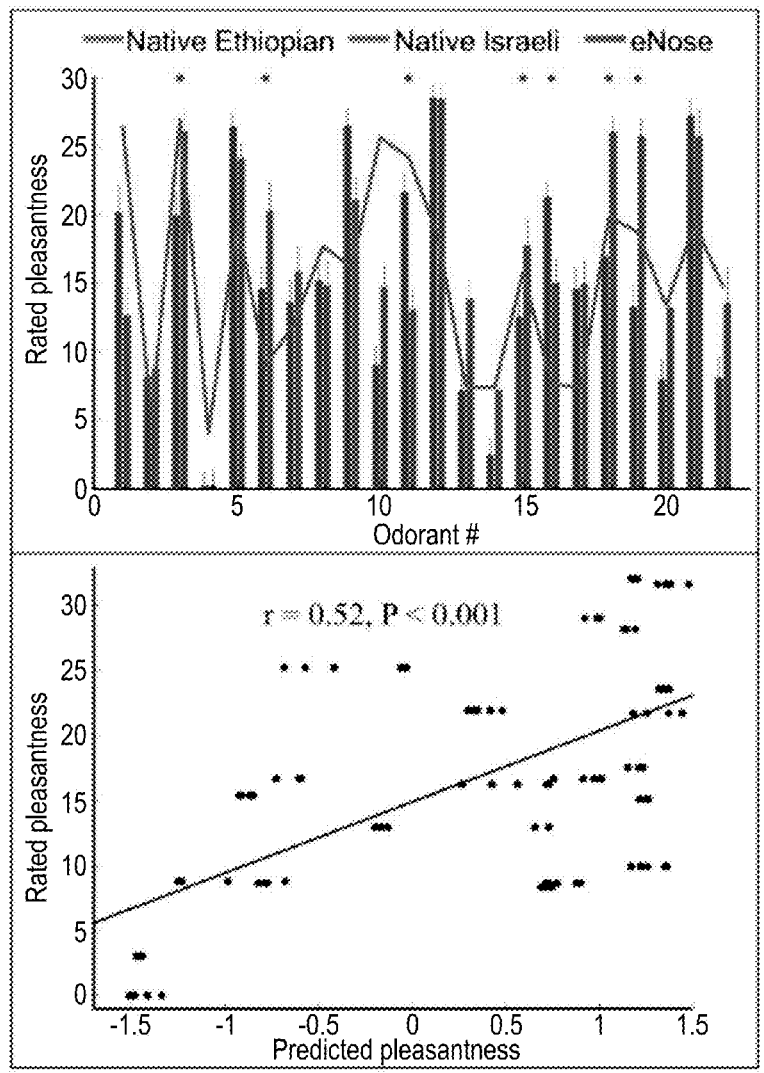

FIGS. 6A-C are three simplified graphs showing a correlation experiment for odors used in the training set, according to an embodiment of the present invention;

FIG. 7A shows graphically a prediction experiment for novel odors, according to an embodiment of the present invention;

FIG. 7B shows graphically the clustering of pleasant and unpleasant odors according to an embodiment of the present invention, when medium odors are removed;

FIG. 8A shows graphically predicted against actual pleasantness of odors in a similar experiment to that shown in FIG. 7;

FIG. 8B shows graphically the same experiment where medium odors are removed, indicating the ability to successfully classify pleasant and unpleasant odors;

FIGS. 9A to 9D show eNose signals of four different odors, those in FIGS. 9A and 9B being considered pleasant, and those of FIGS. 9C and 9D being considered unpleasant;

FIGS. 10A and 10B illustrate a later rerun of the experiment shown in FIGS. 7A and 7B and providing improved results; and FIGS. 11A and 11B illustrate an experiment on odor recognition involving participants from two different cultural groups.

DESCRIPTION OF THE PREFERRED EMBODIMENTS

The present embodiments involve tuning an electronic nose or eNose to human odor pleasantness estimates. The tuned eNose may predict the pleasantness of novel odorants and odorant mixtures, and the predictions are tested in naïve subjects who had not participated in the original tuning experiment. The present embodiments predict the human generated odor pleasantness ratings with ~80% similarity to average human ratings in one experiment and 90% in another. The results are shown to hold true for different cultural groups.

These findings suggest that unlike in vision and audition, in olfaction there is a systematic predictable link between stimulus structure and stimulus pleasantness. This link may provide a critical building block for digital transmission of smell.

The present embodiments thus focus on perceptual axes. Several lines of evidence suggest that the primary perceptual axis of human olfaction is odorant pleasantness. Furthermore, psychophysical evidence suggested that odorant pleasantness is reflected in part in the physicochemical structure of odorant molecules. With this link in mind, we set out to test the hypothesis that an eNose can be tuned to the pleasantness scale, and then used to predict the pleasantness of novel odors.

In an embodiment an axis is defined in which part of the axis is hardwired as unpleasant. In an embodiment parts of the region hardwired to unpleasantness may be related to specific molecules and more particularly to compactness, and to specific compact molecules.

Molecular compactness is an axis of the physicochemical odor world that relates to perception. Compactness is a property that may be computed by applying principal component analysis (PCA) to a list of 1664 molecular features that describe each of 1556 odors. Such PCA may provide a chemical axis that best captures the variance in the world of odor. The importance of this axis is that it can be used to tune odor measuring devices of all kinds (e.g., electronic noses), and tune odor generating devices of all kinds. Thus, if in the future an odor generator is provided as part of a television set or cell phone or computer game or movie theater, etc., than the generator can be tuned according to the axis. Just as a visual projector relies on wavelength and an amplifier relies on frequency, an odor generator may rely on compactness.

One way to characterize such an odor axis is by examining single descriptors that may weight the axis mostly at its ends. We find that these descriptors are associated with atomic (Van der Waals) VDW volumes, atomic polarizabilities, atomic connectivity indices and molecular branching. All these features are correlated with the molecular sparseness/packing level as well as with the molecular accessible surface area. Molecular surface area, in turn, is associated with the molecule's ability to form an induced dipole, and as a result to take part in VDW interactions. Sparse molecules (that are pleasant) are loosely packed, will more readily depolarize in the presence of a local charge or a dipole and therefore tend to take part in VDW interactions. Tightly packed molecules (that are unpleasant), on the other hand, will less likely mobilize their electro-density and will be inert to such weak interactions.

The principles and operation of an apparatus and method according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1:
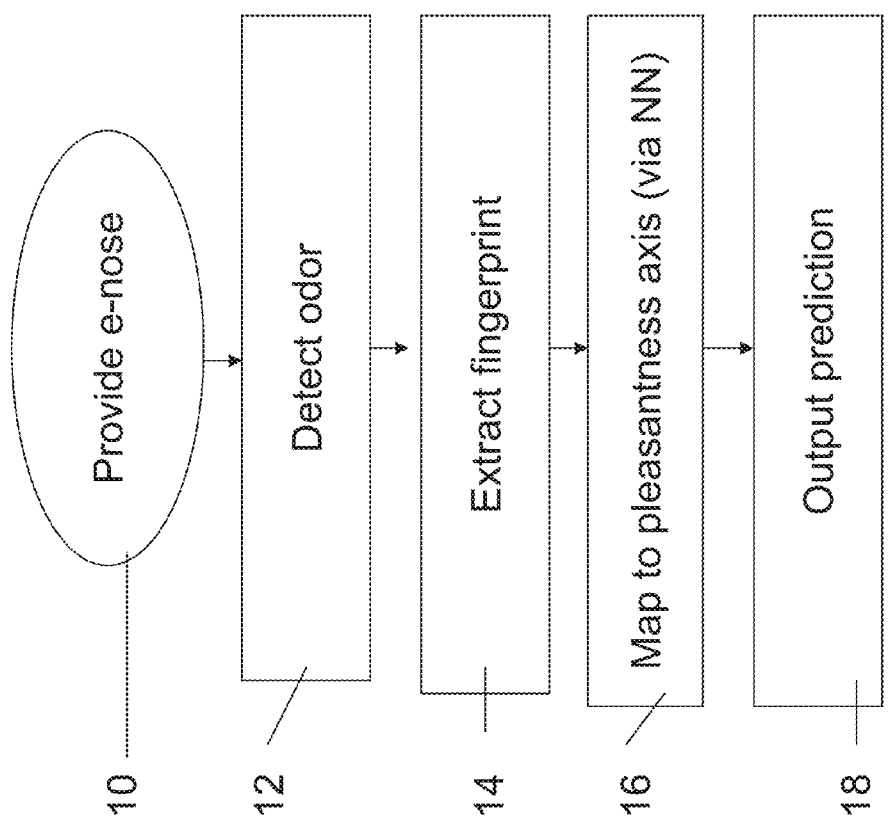

Reference is now made to FIG. 1 which illustrates a method of assessing odors. The method uses an electronic nose to sample an odor—10. The electronic nose samples the odor using non-specific chemical sensors 12, and the output signals of the sensors are processed to find features which characterize the odor 14. Odor information, in the form of a fingerprint or like structure is then mapped onto an axis of odor preference, typically via a neural network but alternatively by any other learning-based mapping feature 16. Finally, an output is provided 18 including an assessment that makes a prediction about how the odor will be experienced by the user. The output is based on the location of the odor in the pleasantness axis.

As well as odor structure features, intensity may be taken into account. The intensity level may also be included in the assessment, so that the same odor at more intense levels may be assessed as being more pleasant or more unpleasant.

The pre-learned axis of odor pleasantness may be obtained by providing a group of assessors with a series of odor samples and obtaining pleasantness scores from each assessor. Each odor may be given an overall score based on the individual assessments. At the same time each odor is analyzed by the electronic nose for the fingerprint or structure of its odor. The scores and the fingerprints are then correlated to form the odor pleasantness axis. Correlating may involve ordering the odor information according to the scores. Typically, a neural network learns to order the odors according to the scores.

The odor information may be obtained from the electronic nose using features of the different odor sensors. This too may be carried out using a neural network, and this would be distinct from a neural network used to correlate odor fingerprints with locations on the pleasantness axis.

The axis of odor pleasantness may comprise structures representing the odor information. Alternatively, if the ordering is done by a neural network then the axis simply is a linear progression of outputs of the neural network.

The method may use the neural network to assess the pleasantness of an odor having a fingerprint not present in the training set. Such an odor is simply passed through the trained neural network to identify a location in the axis.

Figure 2:
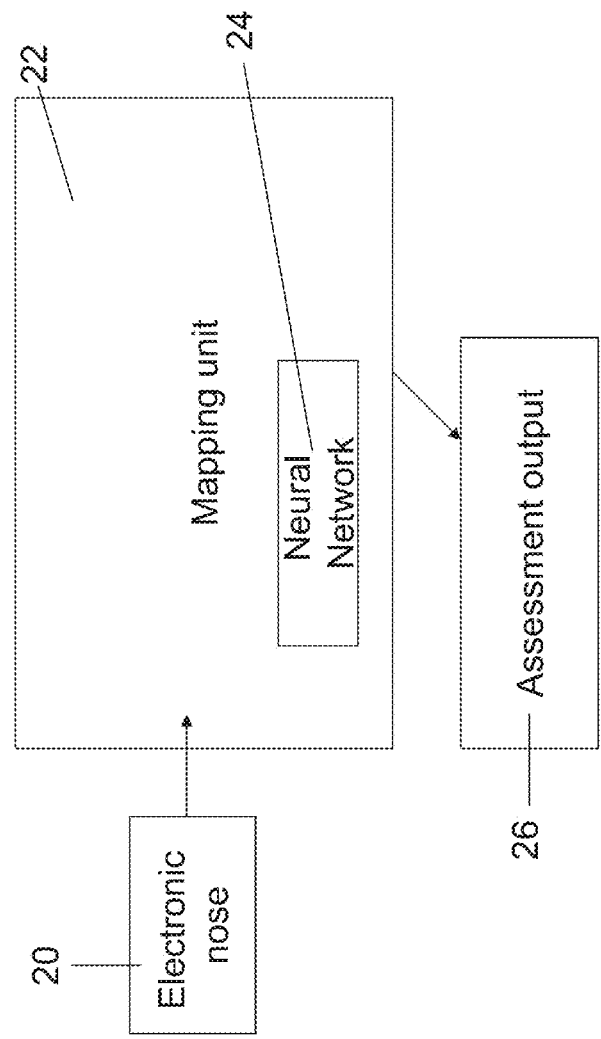

Reference is now made to FIG. 2, which is a simplified block diagram of apparatus for assessing odors according to a preferred embodiment of the present invention. The apparatus comprises an electronic nose 20, which may be applied to an odor and may output a signature, fingerprint or like structure identifying the odor. A mapping unit 22 may plot an extracted structure to a location on the pre-learned axis of odor pleasantness. The plotting unit may make use of or comprise neural network 24 to map signatures of odors to appropriate locations on the axis. Output 26 outputs an assessment of an applied odor based on the location to which the odor is mapped on the axis.

The resultant device was found to provide pleasantness estimates similar to those obtained from human raters, even when using participants and odorants that were not part of the original model building set. This result has implications for biology and biotechnology. For biology, these findings imply a systematic predictable link between odorant structure and odorant pleasantness. For biotechnology, these findings outline a building block for digital transmission of smell. An eNose can use algorithms such as those detailed herein in order to digitize olfactory perception. Such digital representations can then be transmitted, to be either described or recreated at the receiving end.

The pleasantness axis, while not necessary revealing much about the chemical makeup of the odor, provides a reasonable prediction of how a subject may perceive the odor, as will be explained.

We first measured 76 odorants (Supplementary Table 1) with a MosesII eNose. Each odor was measured six times at the same concentration (1 ml of pure odorant), providing 456 samples overall. The MosesII eNose uses 16 different sensors. For each odorant, we extracted 120 features out of the 16 signals, as discussed in the method section below. Of the 420 samples, 32 failed to classify to any of the six repetitions and were removed from further analysis. These failures are believed to relate to the stability characteristics of the Moses II eNose. Thus, the eNose measurements resulted in a matrix of 424×120 (456−32=424). To prevent excessive influence of one sensor over the others, and to minimize the influence of differences in odor vapor concentration that can vary despite equal liquid concentration, we normalized the columns and rows of this matrix. We then asked subjects (15-20 per odor) to rate the pleasantness of each odorant stimuli twice. At this point the odorants were diluted to create iso-intense perception. Rating was carried out using a visual-analogue scale (VAS). Odorants with variance of more than two standard deviations across human subjects were removed from further analysis, and this occurred with 11 of 84 odorants. Using a training set and test set scheme, we trained a neural network algorithm to predict the median pleasantness of the test set. For a test set of 25 odorants, the average correlation between the eNose prediction and the human rating was 0.46 average $P<0.001$, and $P<0.05$ in 95% of the 200 runs.

Figure 3:
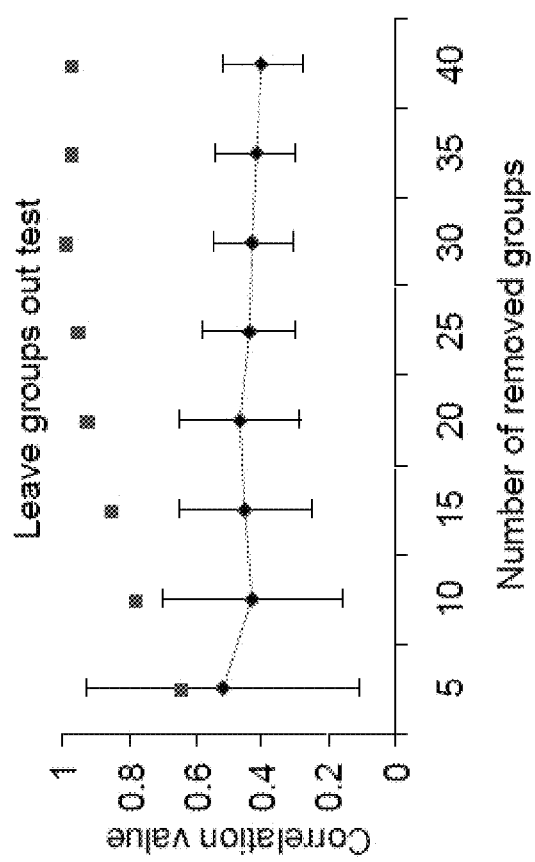

FIG. 3 shows graphically results for prediction of odor pleasantness using an eNose. Correlation values are shown when using different numbers of odorants as test groups. The total number of odorants was 73. The numbers in the abscissa are the number of odorants used as a test set. For each point in the graph, we randomly selected odorants and removed them from the training set. We then trained the eNose using the remaining odorants. We repeated this process 200 times for each group size. The squares mark the percent of times the algorithm obtained $P<0.05$. The circles show the prediction algorithm correlation value obtained and the standard deviation.

In other words, the eNose could predict a proportion of odorant pleasantness within the training set.

FIGS. 6A to 6D show a similar experiment. Referring to FIG. 6A, line 60 indicates correlation values when using different numbers of odorants as test groups and the standard error. The total number of odorants used in this analysis was 76. The numbers in the abscissa are the number of odorants used as a test set. For each point in the graph, we randomly selected odorants and removed them from the training set. We then trained the eNose using the remaining odorants. We repeated this process 20 times for each group size. Line 62 marks the percent of times the algorithm obtained $P<0.05$. Line 64 shows the average P value. Dashed lines 66 and 68 show the same analysis but with an initial training set of 96 odorants (the 74 training set plus the 22 essential oils, see text).

In FIG. 6B, the classification success rate is shown as a function of the odors removed from the test set. Odor rates ranged from 0 to 30. We tested the classification rate when we did not remove any odors (None) and when removed an increasing number of odors. For example, a range removed number of 14-16 represents a test in which we did not consider odors with pleasantness ratings ranging from 14 to 16 (e.g. 1 point below and 1 point above the average ratings). Line 70 indicates the essential oils experiment. Line 72 represents the second 25 odorants experiment.

FIG. 6C shows a power analysis. Line 74 shows he prediction rate (correlation value) versus the number of odorants used in the training set. Line 76 shows the ratio of the number of times the P value was not significant ($P>0.05$). Line 78 shows the mean P value.

Figures 4A, 4B:
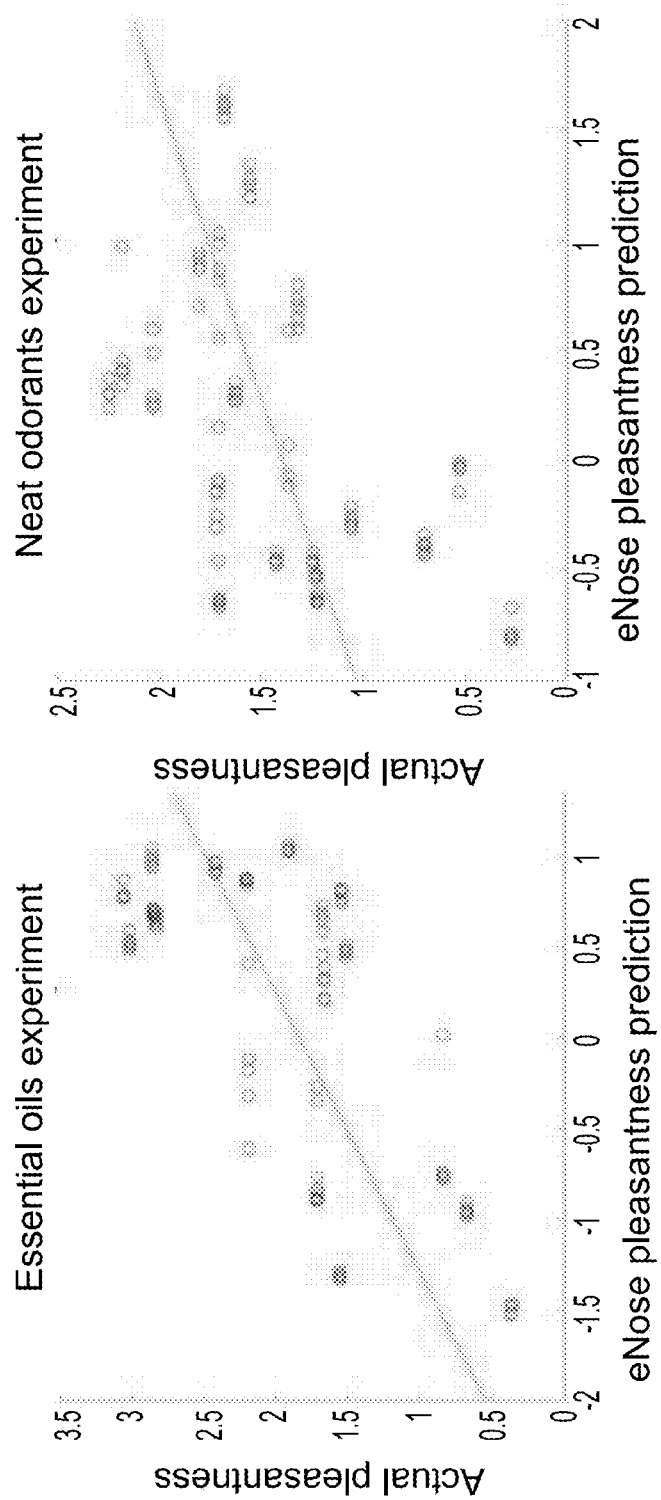

Encouraged by our ability to use an eNose to predict the pleasantness of odorants within the training set, we set out to test its performance with novel odorants, that is with odorants whose signature does not appear in the test set. We used the eNose to measure 22 odor mixtures made of unknown components—see Table 1—essential oils. We measured these oils using the same parameters as in the learning phase, and used the same previously developed algorithm to predict the pleasantness of these odor mixtures. We then asked 15 human participants to rate the pleasantness of these odorants. The correlation between the machine prediction ratings and the human's median ratings was $r=0.58$, $P<0.0001$, and the results are shown in FIG. 4A. We then calculated the average correlation between each human's ratings and the median human's ratings. The correlation was 0.72±0.1, thus the machine-human correlation was 80% of the human to human correlation.

In a further experiment, the results of which are shown in FIG. 7, the correlation between the machine prediction ratings and the human's median ratings over 10 runs was $r=0.64±0.2$, $P<0.0001$ in all 10 runs, and the results are shown in FIG. 7A. We then calculated the average correlation between each human's ratings and the median human's ratings. The correlation was 0.72±0.1, thus the machine-human correlation in this case was 87% of the human to human correlation.

More particularly, FIG. 7A shows the correlation between the eNose pleasantness prediction values of 25 odorants and the values obtained from human participants. FIG. 7B shows An example of the result of the classification algorithm when removing all odorants with medium pleasantness ratings, which are below and above ⅓ and ⅔ of the pleasantness scale respectively.

Although these odors were novel, some of the participants in this study had participated in the original model-building study as well. To address the possibility of any bias introduced by this, we repeated the study again with 17 new participants, and obtained a similar correlation of $r=0.64$, $P<0.0001$. In other words, a machine-human correlation that was 87% of the human to human correlation.

To further test the robustness of our findings, we conducted a third test of our apparatus, using yet another set of 21 novel odorants (Table 1—novel odorants experiment) and a group of 18 new participants. In this case, the human to human group average correlation was 0.55±0.18, and the machine-human correlation was $r=0.45$, $P<0.0001$, in all 10 runs. The results are shown graphically in FIG. 4B, and a similar experiment is shown in FIG. 8A. In other words, the machine-human correlation was 80% of the human-human correlation.

In the experiment shown in FIG. 4B, unlike in the training phase, in all these test experiments we did not remove any odorants, even if they were outliers in either human or machine perception. When we did remove the one outlier in the oils experiment, using the same criterion for outliers as before; there were no outliers in the novel odors experiments, the correlation increased to $r=0.6$, $P<1e-10$.

FIG. 4 is now discussed in greater detail and it graphically shows predicting pleasantness for novel odors. FIG. 4A shows the correlation between the eNose pleasantness prediction values of 22 odor mixtures (essential oils) and the values obtained from human participants. FIG. 4B shows the correlation between the eNose pleasantness prediction value of 21 neat odorants and the actual values as rated by 18 subjects.

FIG. 8A shows the correlation between the eNose pleasantness prediction values of 25 odorants and the values obtained from human participants. FIG. 8B shows an example of the result of the classification algorithm when removing all odorants with medium pleasantness ratings (below and above ⅓ and ⅔ of the pleasantness scale respectively).

Up to this point, we considered a continuous scale of odorant pleasantness. Naturally, the correlation between individual human subjects, as well as between human subjects and machine, was lower for ambiguous or intermediately rated odorants. Therefore, we now set out to ask how the eNose would perform if we restricted our analysis to the very unpleasant or "bad" odors and the very pleasant or "good" odors only.

In this connection, reference is now made to FIGS. 9A to 9D which show the binary cases of very pleasant against very unpleasant odors. In general FIGS. 9A and 9B show four odorant eNose signals of both the QMB sensor module (upper panels) and MOX sensor modules (lower panels). Each line shows the dynamic response of one sensor. Note that both "good" and "bad" odorants generated both strong and weak responses. FIGS. 9A and 9B show two very pleasant odorants. FIGS. 9C and 9D show an example of two very unpleasant odorants.

We conducted a classification analysis after removing odorants with intermediate pleasantness scores (odorants with pleasantness rating ranging from 10 to 20 on the 30 point scale). We classified odorants as pleasant if their predicted pleasantness value was above zero, and unpleasant otherwise. Strikingly, the eNose discriminated between the two odor groups with 99% accuracy (FIG. 6B, line 70 and FIG. 7B. We repeated this analysis on the second set of 25 odorants and 18 participants, and obtained a discrimination success rate of 90% (FIG. 6B, line 72 and FIG. 3B). Considering the known relation between odor intensity and odor pleasantness, it is noteworthy that this categorical discrimination of very pleasant from very unpleasant odorants could not have depended on the magnitude of the eNose response alone. This is because the analysis was conducted using the normalized eNose values, and perceptually iso-intense odorants. It is noted that there was no significant correlation between odor intensity and pleasantness in the two test experiments: $P=0.51$ and $P=0.08$; $|r|<0.35$ in both. Moreover, examination of the raw eNose response suggested that odorant pleasantness was not a reflection of eNose response magnitude even in the prenormalized state (FIG. 9). We conclude that our apparatus discriminated good odors from bad odors, and that this prediction power was not based on odor intensity.

To test the dependence of our algorithm on the training set, we repeated the tests for each of the two novel odor experiments while augmenting the training data with the other odor set. The results remained similar: $r=0.52$, and $r=0.43$ respectively ($P<0.0001$ for both). In other words, the prediction was not a result of using a specific training set under specific training parameters.

To farther test the power of this algorithm we repeated the leave group out test while augmenting the training set with the essential oils data. This experiment is represented by dashed line 80 in FIG. 6A. As can be seen the prediction accuracy improved for increased size of training set. One can thus ask, what was the relation between the training set size and the prediction accuracy, or in other words, how many odors should we present the eNose before we can start predicting? Line 74 in FIG. 6C indicates that the prediction attained significance after 30 samples and entered saturation after 60-70 samples.

Reference is now made to FIG. 3 which likewise graphically illustrates prediction power analysis of the present device.

Figure 5:
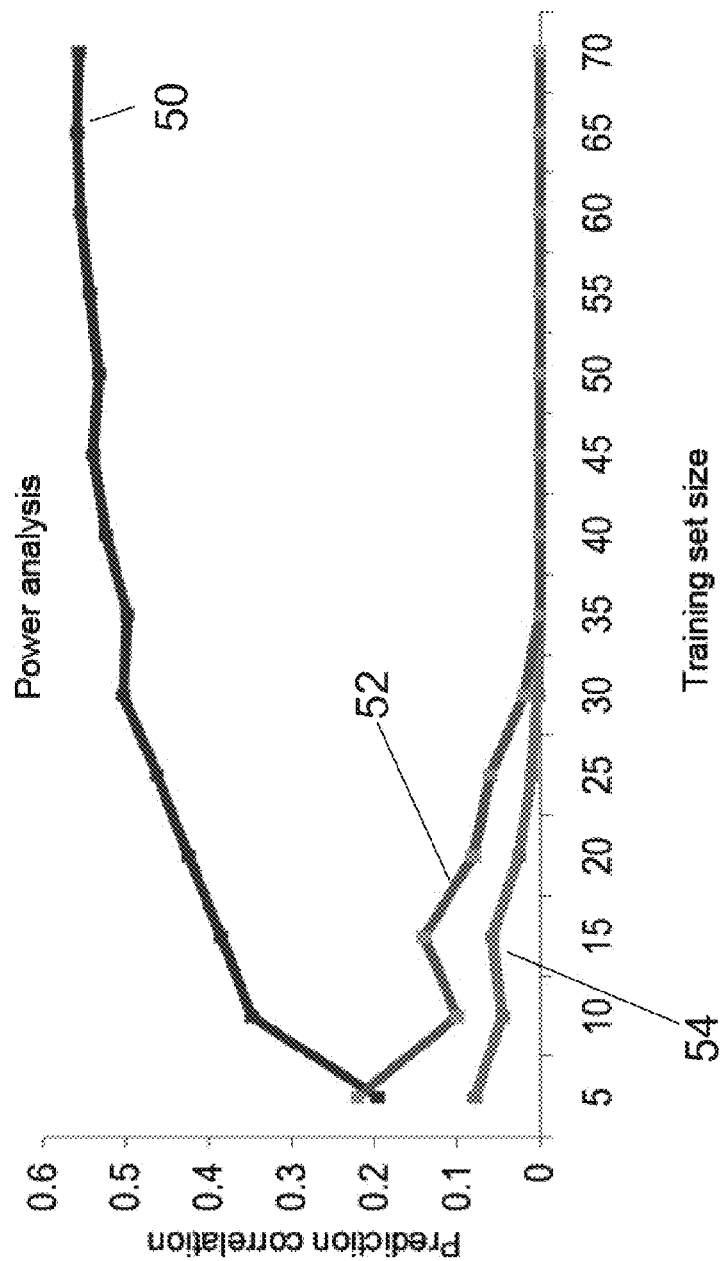

Line 50 illustrates the prediction rate (correlation value) versus the number of odorants used in the training set. Line 54 illustrates the ratio of the number of times the P value was not significant ($P>0.05$). Line 56 illustrates the mean P value as a function of the number of training sets As can be seen in FIG. 5 line 50 shows that the prediction obtained significance with only 25 samples and saturated with 60-70 samples. Based on this analysis we suggest that around 50 samples are required to predict odour pleasantness with reasonable accuracy using this eNose setup.

To farther test the dependence of our algorithm on the identity of odorants in the training set, we repeated the tests for each of the two novel odorant experiments while augmenting the training data with the other odorant set. The results remained similar: $r=0.62$ ($P<0.0001$) and 95% classification rate in the essential oils experiment and $r=0.47$ ($P<0.0001$) and 90% classification rate in the neat odorants experiment (when removing odorants ranging from 10 to 20 pleasantness ratings). In other words, the prediction was not a result of using a specific training set under specific training parameters.

Finally, to farther probe the statistical robustness of the results, we scrambled our pleasantness data in a pseudorandom fashion 100 times and repeated our prediction analysis. The average prediction rates dropped to $r=0.08$, $P>0.23$. In other words, the predictions obtained were not due to some internal structure of the data but rather reflected the ability of the algorithm to predict odor pleasantness.

A Turing test, the benchmark for artificial intelligence, holds that if by communication a person cannot determine whether their machine interlocutor is machine or human, then the machine is intelligent. This concept was extended to simulating natural systems in general, where a simulated natural system may be considered complete if a human expert cannot distinguish the simulation from the real system in a reliable manner. Machines can pass a Subject Matter Expert Turing Test when it is restricted to rule based cognitive systems such as games, or perceptual tasks such as category learning. For example, software can generate ratings of facial attractiveness similar to those obtained from human raters. However, such results were limited to strict acquisition parameters (same facial pose, illumination, etc.), and unlike our results, such achievements did not generalize beyond the test set. Furthermore, no software can currently tell us whether a human would like a novel image containing more than faces alone. Similarly, a musical peace can be recorded, digitized and transmitted. Whereas software at the receiving end may be able to rate its appeal for previously characterized listeners, it would not be able to tell us whether a person whose personal preferences were not previously characterized would like the music had they heard it. This is because hedonics, the perceptual range from pleasant to unpleasant, is far removed from the structure of the stimulus in these sensory domains. In contrast, the primary perceptual axis of olfaction is hedonics, and the degree of odorant pleasantness is in part written into the atomic structure of the stimulus in a predictable manner. With this in mind, we hypothesized that a machine could sample an odor, the sample could be digitized and transmitted, and in contrast to vision and audition, software at the receiving end could tell us whether the odor was pleasant or unpleasant. Our results support this hypothesis, and thus may be considered as passing a weak form of olfactory Turing test. In this respect, it is noteworthy that the proportion of variance in pleasantness predicted by the eNose (r=~0.5) was nearly identical to the proportion of variance in pleasantness that can be predicted from physicochemical structure (r=~0.52).

It is noted that a proportion of odor pleasantness is likely dependent on culture. Although the extent of this proportion is unclear, this nevertheless suggests that inter-cultural eNose predictions of odorant pleasantness will be weaker than intra-cultural predictions like those conducted here. Second, odorant pleasantness is related to odorant concentration. Here we negated this source of variance by using equal concentrations across odorants for the eNose measurements, and equal perceived intensities across raters for the human perception measurements. An alternative algorithm may account for concentration-dependent shifts in pleasantness. Thus, when we increased the training set size as per the dashed lines in FIG. 6A the correlation value increased substantially to give r=0.56, P<0.0001. Thus despite limitations, the device of the present embodiments discriminated very pleasant odors from very unpleasant odors with high accuracy in both the novel odorants and odorant mixtures experiments (90%-99%). Thus, this suggested apparatus can be used for fast odor, which is a task currently performed by human panels and for environmental monitoring, which is a task currently conducted by applying specific sensors that can detect only specific preidentified chemicals.

Finally, these results may be considered a building-block for digital communication of smell. Individual smells are often composed of thousands of different molecules, each at a particular ratio. Deciphering the exact composition of such odors is a daunting prospect, and recreating these exact mixtures is currently technically limited. In turn, the direction we point towards here is to decipher the odorant-score along main perceptual axes of smell. Once an odorant is characterized along several key axes, a dispensing machine may be able to generate a stimulus defined by the resultant axes-space, an odorant that even if not identical, would nevertheless generate a similar percept.

Materials and Methods eNose Measurements:

The MOSES II eNose we used contains eight metal-oxide (MOX) sensors and eight quartz microbalance (QMB) sensors. MOX and QMB are two very different sensor technologies that together capture many facets of the ligand's nature.

The 1 ml (without any dilution) samples were put in 20-ml vials in an HP7694 headspace sampler, which heated them to 50° C. and injected the headspace content into the MOSESII with a flow rate of 40 ml/liter. These parameters maximized the number of chemicals that elicited a strong response. To avoid the problem of conditioning we put a blank vial before every measurement and we cleaned the system using steamed air after each run. Each analyte was first introduced into the QMB chamber, whence it flowed through to the 300° C. heated MOX chamber. The injection lasted 30 seconds, and was followed by a 20 minute purging stage using clean air. Each chemical was measured six times over a period of several days. In total, we performed 456 measurements. Each odorant was measured at the same level of humidity and temperature. Each single measurement consisted of sixteen time-dependent signals, corresponding to the eNose sixteen sensors.

eNose Signal's Feature Extraction Methods

From each of the 16 sensor signals we extracted four parameters. These parameters were: the signal max value and latency to max, the time the signal reaches the half max value on the decay part and on the rise part. In many cases the signal max value can change considerably between measurements of the same odorants, however, the relative height of the 8 sensors in each of the two sensor modules was largely maintained. Thus, to capture this behaviour we added to each odorant representation the 28 possible ratios of the 8 MOX signals and 28 ratios of the 8 QMB signals. We thus ended up with 120 features for each odorant. To ask whether this feature extractions method was a good representation of the odorants, we clustered the 420 eNose measurements we had into the 84 odorant classes and tested how many odorants fail to cluster into their odor class. Out of the 420 measurements 89% clustered correctly. We removed the 11% signals that failed to cluster to their class. After this signals removal, we ended up with 3 to 5 repetitions per sample measured. We normalized both the feature values and the odorant signature thus removing bias to specific sensor type and odor concentration respectively.

Human Estimates:

Subjects 56 healthy normosmic subjects (31 females) ranging in age from 23 to 54 years participated in the study. Subjects were paid for participation. A second group of 31 healthy normosmic native born Ethiopian subjects including 24 females, also participated. They ranged in ages form 20-37 years and arrived in Israel between 1 and 5.5 years prior to testing with a mean of 2.3 years.

Odor Ratings

The total of 123 odors (the 76 training odors and the 47 test odors) were divided into groups of 20-25 odors each. This grouping reflected the maximal time a human subject will typically consistently rate odors (~40 minutes, with at least 30 seconds between odorant presentations). All odors were first individually diluted to be perceptually equi-intense. Each group of odors was then rated by 15 to 21 subjects. Each subject ranked the pleasantness and intensity of each odor on a visual analogue scale. Each odor was randomly presented twice to each subject. In total, for each odor more than 30 ratings were obtained, and a few of the subjects decided that they did not want to rate for the second time. The pleasantness of an odor was calculated by taking the median of all subject's ratings.

Between and Within Odor Rating Correlations

To estimate human to human ratings we calculated the Pearson correlation between all subject pairs and calculated the average correlation value (n>100). To verify that our results were not biased due to the use of visual analogue scale (VAS) we ran an additional experiment using 21 odorants with 6 subjects using a 7 category rating experiment. The categories offered to the subjects were: The worse odor you ever smelled, very bad, bad, Ok, good, very good, the best odor you have ever smelled. The between human correlation was similar (r=0.57 in the category rating experiment versus r=0.6 in the VAS rating experiment; P<0.01 in both). Overall, when considering all our humans ratings, the human to human correlation was 0.45±0.18 (P<0.01) and human to the human group average correlation was 0.67±0.12 (P<0.01). Calculating the average correlation of each subject first rating to his second rating we obtained r=0.73±0.15 (P<0.01).

Modeling

We used Matlabs' implementation of a three layered feedforward back-propagation neural network with 5 internal neurons and 20 epochs. Changing the number of neurons or epochs in the range of 3-10 and 10-30, respectively, did not change the result. The layers' transfer functions were 'tansig' and 'purelin'. The training function was 'traingd'. To calculate the prediction we ran the algorithm 20 times and used the average value as our best predictor.

Classification Algorithm

To classify odors we used the same algorithm we used for the prediction. Odors with positive predicted value were classified as pleasant and odors with negative predicted value were classified as unpleasant.

Additional Experiments

Reference is now made to FIGS. 10A and 10B which are a later attempt at the experiment shown in FIGS. 7A and 7B. Correlation is shown between the eNose pleasantness prediction values of 21 odorants and the values obtained from human participants. Each dot represents an eNose measurement and many dots overlay. FIG. 7B shows the result of the classification algorithm when removing all odorants with medium pleasantness ratings, that is those below and above ⅓ and ⅔ of the pleasantness scale respectively.

Reference is now made to FIG. 11, which illustrates cross-cultural validation of the correlation results. In FIG. 11A, odorant-specific pleasantness ratings for native Ethiopians (blue), native Israelis (brown), and eNose (pink). The blue stars on the upper x axis denote the 7 odorants where native Ethiopians and native Israelis significantly differed in their pleasantness ratings. Note that for odors #6 #18 and #19 the pink line (eNose) is in fact closer to the native Ethiopians than to the native Israelis even though the eNose was tuned on a separate group of native Israelis. FIG. 11B. shows the correlation between the eNose pleasantness prediction values of 22 odorant mixtures (essential oils) and the values obtained from native Ethiopians. Each dot represents an eNose measurement (many dots overlay). Comparing FIG. 7a to FIG. 11b reveals that native Israeli participants rated more at the middle of the VAS scale and native Ethiopians rated more at the scale extremes.

Considering the additional experiments in greater detail, up to this point, we had considered a continuous scale of odorant pleasantness. Naturally, the correlation between individual human subjects, as well as between human subjects and machine, was lower for ambiguous or intermediately rated odorants. Therefore, we now set out to ask how the eNose would perform if we restricted our analysis to the categorically pleasant and unpleasant odors.

We conducted a classification analysis after removing odorants with intermediate pleasantness scores (odorants with pleasantness rating ranging from 10 to 20 on the 30 point scale). We classified odorants as pleasant if their predicted pleasantness value was above zero, and unpleasant otherwise. Strikingly, the eNose discriminated between the two odor groups with 99% accuracy. We repeated this analysis on the second set of 21 odorants and 18 participants, and obtained a discrimination success rate of 89%. Considering the known relation between odor intensity and odor pleasantness it is noteworthy that this categorical discrimination of very pleasant from very unpleasant odorants could not have depended on the magnitude of the eNose response alone. This is because the analysis was conducted using the normalized eNose values, and perceptually iso-intense odorants (there was no significant correlation between odor intensity and pleasantness in the two To test experiments: P=0.51 and P=0.08; |r|<0.35 in both). To reiterate: the odorants were diluted to an equated perceived intensity before their pleasantness was rated by humans. Moreover, examination of the raw eNose response suggested that odorant pleasantness was not a reflection of eNose response magnitude even in the pre-normalized state. We conclude that our apparatus discriminated pleasant odorants from unpleasant odorants, and that this prediction power was not based on odorant intensity.

Cross-cultural validation: A portion of human olfactory perception is modified through cultural context, and learning. Although the extent of this portion remains unclear, this nevertheless raises the possibility that the performance of our apparatus was culture-specific. To address this, we set out to test the performance of our apparatus in a group of recent immigrants to Israel from rural Ethiopia. The native Ethiopian participants were adults (mean age=27) who had arrived in Israel on average 2.3±0.8 years before testing. Because the significant assimilation facing these immigrants in their passage from rural Ethiopia to modern Israel entails a long-term process, this group was all still living together as an independent community in an Israeli Absorption Center where we conducted the experiment. Ethiopian scent-culture is unique in many ways, and therefore these participants provided an ideal test for the cultural dependence of our apparatus. Critically, we tested our apparatus with these participants without re-learning or re-calculating any of the apparatus parameters.

Interestingly, despite co-author AM's fluent Amharic, we encountered difficulty in conveying the notion of a visual-analogue rating scale to the native Ethiopian participants. That is, the native Ethiopian participants tended to rate odors at the extremes of the scale, and made lesser use of the middle range. This was made evident in the standard deviation of the VAS scale values. Whereas the average standard deviation of the mean across the same odorants in the native Israeli participants was 6.1±1.5, the average standard deviation of the mean in the native Ethiopian participants was 8±1.5 (T(21)=5.4, p<0.00002).

The correlation in pleasantness ratings between native Ethiopians and native Israelis was r=0.75 (p=0.00004). Although across all odors the median pleasantness assigned by native Ethiopians (14.9±6.5) was not significantly different from the native Israelis (16.7±6.6) (t(21)=1.8, p=0.08), when looking at each odorant separately, this group was significantly different from the native Israelis in its pleasantness rating of 7 odorants, 2 of which were rated as significantly more pleasant by native Ethiopians, and 5 of which were rated as significantly less pleasant (FIG. 5A). Finally, there was no correlation between the time since arrival in Israel and similarity in rating between the native Ethiopian immigrants and native Israelis (r=−0.17, p=0.82), suggesting that the native Ethiopian participants remained a homogenous group from the perspective of our question.

The average correlation between the machine prediction ratings and the native Ethiopian's median ratings was r=0.52±0.01 (P<0.001) (FIG. 5B). This correlation was not significantly different from the correlation previously obtained in native Israelis (Fisher z=0.69, p=0.49). Furthermore, the correlation between each native Ethiopian's ratings and the median native Ethiopian rating was 0.60±0.2, thus the machine-human correlation was 86% (0.52/0.60*100=86) of the human-to-human correlation in the native Ethiopian population. In other words, the eNose performed equally well across cultures.

Finally, because of the standard deviation in VAS scale usage by the native Ethiopian participants, a classification analysis of extremely pleasant versus extremely unpleasant odorants similar to that conducted in the native Israelis is less informative in this case. Put simply, these participants rated nearly all odorants as extremely pleasant or extremely unpleasant, rendering a classification analysis similar to a simple correlation analysis. Nevertheless, we conducted a classification analysis as well, and the eNose discriminated between the two odor groups with 69% accuracy (p<0.0001).

Because the native Ethiopians and native Israelis significantly differed in their pleasantness ratings for only 7 odorants, this is too small a subgroup for independent statistical analysis. However, a descriptive observation of this subset of odorants remains informative in that for several of the odorants with significant differences, the eNose prediction was in fact closer to the estimates of the native Ethiopians than to the estimates of the native Israelis (e.g., odorants #6, 18 and #19 in FIG. 5A). This suggests that although the eNose was initially tuned using an independent group of native Israelis, it nevertheless captured a culture-independent aspect of molecular structure that predicts pleasantness.

eNose algorithm power analysis: To test the dependence of our algorithm on the size of the training set, we repeated the leave-group-out test while augmenting the training set with the essential oils data. When the training set was larger the prediction accuracy improved. To quantify this relationship, we asked what was the relation between the training set size and the prediction accuracy, or in other words, how many odorants should we present the eNose before we can start predicting? The prediction obtained significance with only 30 samples and saturated with 60-70 samples. Based on this analysis we suggest that around 50 samples are required to predict odor pleasantness with reasonable accuracy using this eNose setup.

Finally, to ask whether our results were significantly impacted by our outlier removal criteria for eNose measurements, we repeated the correlational analysis using all the data with no exclusions. This resulted in a minimal reduction in correlation between eNose and human pleasantness rating from $r=0.64$ to $r=0.62$, and this correlation remained highly significant ($p<0.0004$). We also repeated the classification analysis with inclusion of outliers, and classification accuracy remained the same (99%). We conclude that our results were not significantly influenced by outlier removal.

Thus overall results show above 90% accuracy at discriminating between categorically pleasant or unpleasant odorants. Similar results are obtained in two cultures, native Israeli and native Ethiopian, without any need for retuning of the apparatus.

In the present embodiments, we eNosed, digitized, and transmitted to receiving software, the smell-print of novel odorants, and in contrast to vision and audition, could predict their pleasantness with accuracy similar to that of a novel smeller. In other words, we could predict whether a person who we never tested before would like the odorant, and this prediction was consistent across Israeli and Ethiopian cultural backgrounds.

We argue that this difference was not a reflection of better hardware (in fact, an eNose is less precise than a modern camera or sound recorder), or better algorithms, but rather a reflection of a fundamental biological property of the sense of smell. These findings imply that unlike in vision and audition, in olfaction pleasantness is written into the molecular properties of the stimulus, and is thus better-captured by a machine.

It is tempting to speculate as to the specific molecular aspects that our apparatus was most sensitive to in its determination of pleasantness. For example, careful review of the experimental data reveals that many low pleasantness odorants were either carboxylic acids or amines, suggesting a functional group specificity. However, other unpleasant odorants, e.g., cyclohexanol, belonged to different functional groups. Previously, we have described a physicochemical odorant axis that corresponds to odorant pleasantness (PC1 of physicochemical structure in Khan et al., 2007). If forced to choose a single verbal label that best describes this axis, one might choose compactness, where increased molecular compactness infers reduced odorant pleasantness. We cannot yet determine, however, whether our apparatus was transducing molecular compactness, or functional group, or some other physicochemical aspect. That said, that the apparatus could nevertheless predict pleasantness across cultures further strengthens the link between odorant pleasantness and odorant structure.

This finding of hard-wired odorant pleasantness is in contrast to the popular notion that odorant pleasantness is both subjective and learned. We argue that in this respect olfactory pleasantness can be likened to visual color. Most would agree that color is hard-wired to wavelength within a predictable framework. That said, color perception can be influenced by culture, and context, as well as by learning and memory. All this does not detract from the hard-wire link between perceived color and wavelength. Similarly, we argue that olfactory pleasantness is hard-wired to molecular structure. That this link is modified through culture, context, and learning, does not preclude the initial hard-wire aspects of this link, and it is this link that we have captured. Indeed, it is thanks to such hard-wiring that rodents bred for generations in predator-free laboratories are nevertheless averse to the smell of predators, human newborns with no exposure to culture or learning are nevertheless averse to unpleasant odorants, and that when tested out of context, odorant pleasantness is relatively constant across cultures as revealed here. To stress this point, we predict that if our odorants were presented to subjects within context, e.g., in foods, than the native Israeli and native Ethiopian participants may have then diverged in their pleasantness ratings. For example, peppermint may be rated as a pleasant smelling food in only one of two cultures. However, both cultures may then find peppermint equally pleasant when presented out of context in a jar. Indeed, many may wonder how the French can like the smell of their cheese. However, it is not that the French think the smell is pleasant per se, they merely think it is a sign of good cheese. To prove the point: the French don't make cheese smelling perfume! In other words, culture influences olfactory hedonics mostly in particular contexts. When out of context, odor pleasantness is less culturally variable, and we argue that it is this context-free component that was captured by our apparatus.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of assessing odors, comprising:
providing an electronic nose;
applying said electronic nose to an odor;

extracting odor information of said odor using said electronic nose;

plotting said extracted odor information to a first location on an axis of odor pleasantness via learning-based mapping, said axis of odor pleasantness comprising odor points ordered for pleasantness between a first high pleasance end and a second low pleasance end of said axis; and outputting an assessment based on said first location.

2. The method of claim 1, wherein said axis of odor pleasantness comprises a linear succession of mappings of odor signatures to gradings of pleasantness.

3. The method of claim 1, comprising providing said learning-based mapping for said axis of odor pleasantness by:

providing assessors with a series of odor samples;

obtaining pleasantness scores from each assessor;

extracting odor information of said samples using said electronic nose; and training to correlate said scores with said extracted odor information by mapping said odor information to a linear succession of said scores.

4. The method of claim 1, wherein said odor information is obtained within said electronic nose by extracting features from signals output by sensors of said nose.

5. The method of claim 4, further comprising minimizing said features to a minimal set that allows convergence of same odors and divergence of different odors.

6. The method of claim 5, comprising assessing the pleasantness of an odor having odor information not used in training, by mapping to said axis using said mapping.

7. The method of claim 1, further comprising hardwiring a region of said axis to an indication of unpleasantness.

8. The method of claim 7, comprising associating parts of said region with respective predetermined compact molecules.

9. The method of claim 1, comprising setting up said axis according to measures of molecular compactness.

10. Apparatus for assessing odors, comprising:

an electronic nose, configured to be applied to an odor and to output a structure identifying said odor;

a learning based mapping unit, attached to an axis of odor pleasantness, said mapping unit pretrained with odors and corresponding pleasantness gradings, configured to map an extracted structure to a first location on said axis of odor pleasantness, said axis of odor pleasantness comprising odor points ordered for pleasantness between a first high pleasance end and a second low pleasance end of said axis; and an output for outputting an assessment of an applied odor based on said first location.

11. Apparatus according to claim 10, wherein said axis of odor pleasantness comprises a linear succession of mappings of odor signatures to gradings of pleasantness.

12. Apparatus according to claim 10, wherein said axis of odor pleasantness comprises a plurality of structures from test odors ordered according to assessments of pleasantness provided by assessors.

13. Apparatus according to claim 10, wherein said structure is obtained within said electronic nose using signal output features of sensors of said electronic nose.

14. Apparatus according to claim 10, wherein said structures represent odor information of chemical content of said odors according to a plurality of non-specific chemical sensors.

15. Apparatus according to claim 14, wherein said learning based mapping unit is configured to plot a structure not present in said axis, by comparing with closest structures in said axis, thereby to identify a respective first location.

16. Apparatus according to claim 10, further comprising a region of said axis being hardwired to an indication of unpleasantness.

17. Apparatus according to claim 16, comprising parts of said region associated with respective predetermined compact molecules.

18. Apparatus according to claim 10, wherein said axis is calibrated according to measures of molecular compactness.

19. A method of assessing odors, comprising:

providing an electronic nose;

applying said electronic nose to an odor;

extracting odor information of said odor using said electronic nose;

plotting said extracted odor information to a first location on an axis of odor pleasantness via a learning-based mapping unit;

minimizing features extracted from sensors of said electronic nose to a minimal set that allows convergence of same odors and divergence of different odors;

assessing the pleasantness of an odor having odor information not used in setting up said learning based mapping unit, by mapping to said axis using said learning-based mapping unit; and outputting an assessment based on said first location.

20. A method of assessing odors, comprising:

providing an electronic nose;

providing an axis of odor pleasantness by ordering odor points for pleasantness between a first high pleasance end and a second low pleasance end of said axis and hardwiring a region of said axis to an indication of unpleasantness;

applying said electronic nose to an odor;

extracting odor information of said odor using said electronic nose;

plotting said extracted odor information to a first location on said axis of odor pleasantness via a learning-based mapping unit; and outputting an assessment based on said first location.

* * * * *